United States Patent [19]

Laarhoven et al.

[11] Patent Number: 4,492,867
[45] Date of Patent: Jan. 8, 1985

[54] METHOD OF AND APPARATUS FOR DETERMINING THE STATE OF AGEING OF PLASTIC PRODUCTS

[75] Inventors: Johannes J. Laarhoven, Hardenberg; Jan P. van Dongeren, Bergentheim; Hendrik de Wit, Wassenaar; Louis M. Smeets, Amsterdam, all of Netherlands

[73] Assignee: Wavin B.V., Zwolle, Netherlands

[21] Appl. No.: 398,235

[22] Filed: Jul. 14, 1982

[30] Foreign Application Priority Data

Jul. 5, 1981 [NL] Netherlands .......................... 8103468

[51] Int. Cl.³ ............................................... G01J 1/00
[52] U.S. Cl. .................................................... 250/341
[58] Field of Search ............... 250/338, 340, 341, 339, 250/358.1, 359.1

[56] References Cited

U.S. PATENT DOCUMENTS

| | | | |
|---|---|---|---|
| 3,524,983 | 8/1970 | Voelz | 250/341 |
| 3,631,526 | 12/1971 | Brunton | 250/341 |
| 3,783,284 | 1/1974 | McCormack | 250/341 |
| 4,017,194 | 4/1977 | Conroy et al. | 250/341 |

Primary Examiner—Janice A. Howell
Attorney, Agent, or Firm—Wilkinson, Mawhinney & Theibault

[57] ABSTRACT

In a non-destructive method the state of ageing of plastic products is determined by means of infrared radiation, which is passed through the product.

The invention is based upon the discovery that there is a clear relationship between certain physical and/or chemical changes occurring during the course of time in the interior of plastic materials, detectable by infrared analysis, and the mechanical properties of the product. On the basis of this relationship, the method may be used to decide whether products can be safely used or whether they must be disqualified and removed.

The method is particularly well suited with crates which are to contain bottles; the radiation is then passed through a crate wall.

Apparatus for performing the method may be arranged in a line such as a conveyor belt bottling line.

16 Claims, 4 Drawing Figures

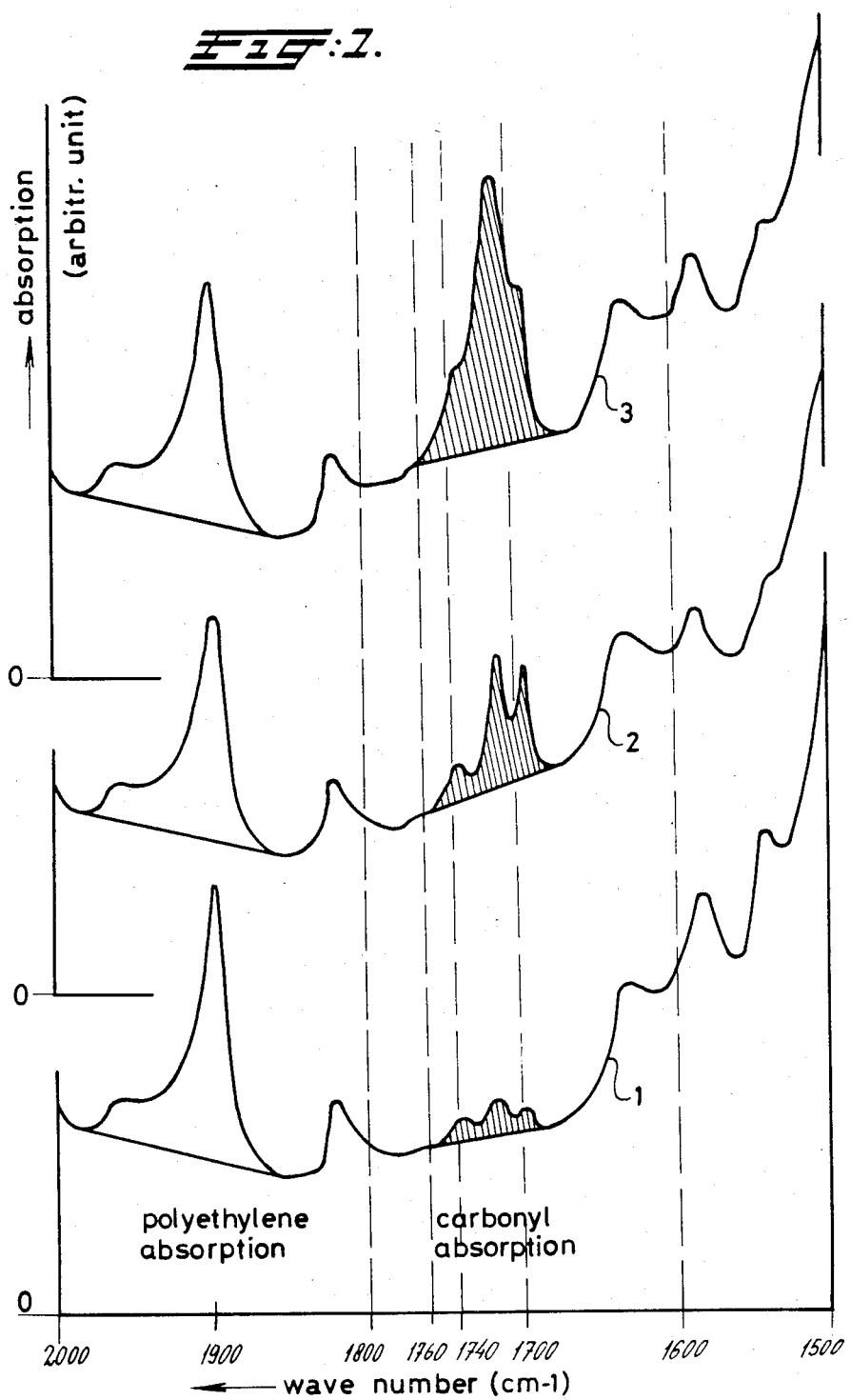

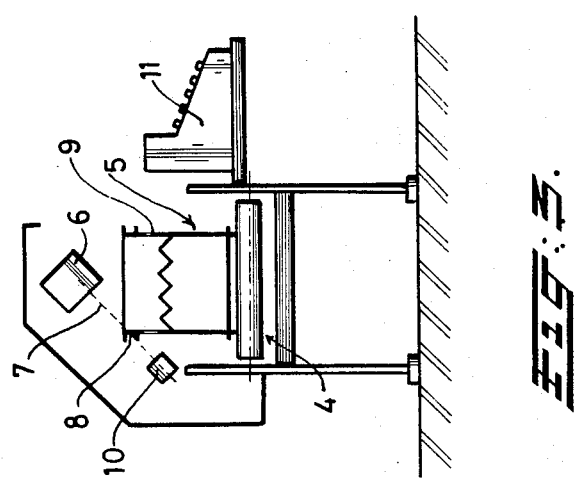
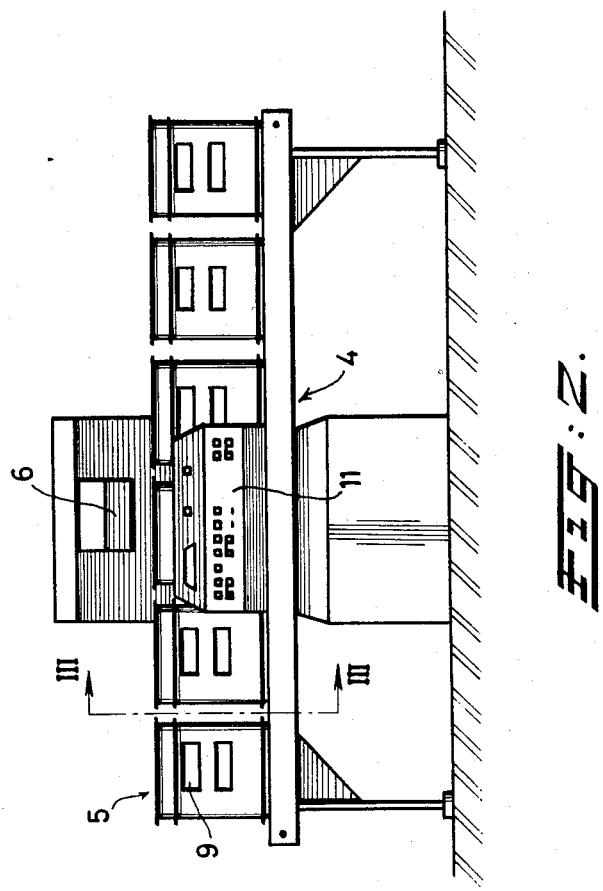

METHOD OF AND APPARATUS FOR DETERMINING THE STATE OF AGEING OF PLASTIC PRODUCTS

BACKGROUND OF THE INVENTION

1. Field of the Invention

The invention relates to a method of determining the state of ageing of plastic products.

2. Description of the Prior Art

It is of importance to know the state of ageing of certain plastic products, for example, crates, because the material may age so far that the product, also in normal use, does no longer meet the requirements for use. When such products could be signaled, there is a possibility to select and to remove them.

Products, which are being used a long time in great quantities, even if apparently they are identical, need not always be really qualitatively equivalent. With products, such as the abovementioned crates, which are used for packing bottles containing beverages, it is usual to add, during the course of years, new items, both by expansion and by replacement of products which got lost; in practice the products of various ages are intermingled. Although visually it is difficult to discern them, part of them may have become imperfect.

For the deterioration of quality, various causes are known, such as ultraviolet radiation, high temperatures and internal instability of the material. It is important to distinguish early those products which have aged too far because otherwise, by breaking down during use or in operation, danger for man and/or environment may arise.

Visual selection is very unreliable anyhow. Another known method of determining the state of ageing is the determination of the values of the impact strength by means of little test bars. This method is reliable, but for the test the product must be destroyed. There are several of these test methods which all are destructive.

Also known is the method in which, by means of infrared radiation, an analysis is made of a very small quantity of material scraped off from the product. This method presupposes that the deterioration of the product quality results from a change in the material, and it is known that these changes in the surface of the material produce a different absorption for infrared radiation than the "good" material. For this method of investigation a thin layer is scraped from the surface. The method is not destructive, but the test takes a lot of time and is therefore poorly suited for a continuous check in a factory in which one works with the products, in view of being able to continuously remove the aged products.

OBJECTS OF THE INVENTION

The invention wants to present a solution to this problem and its first object therefore is to provide a method, and an appropriate apparatus as well, with which in a very simple and quick manner, a check can be made continuously.

Another object is to privide an apparatus for infrared analysis which is suitable to be installed in regular lines such as a bottling line.

SUMMARY OF THE INVENTION

According to the invention, infrared radiation is passed through the product, the absorption in the material is determined and said absorption is utilized as a criterion for the state of ageing.

Thus, the invention is based upon the surprising discovery that also internally in the material ageing phenomena may occur, which can be detected by means of infrared analysis. It turns out generally, namely, that all plastic materials, in an infrared area having wave numbers between 200 and 4000 cm$^{-1}$, present an absorption spectrum in which, during the course of time, changes occur. Furthermore, it has turned out that these changes in the material have a direct relationship with the mechanical quality which is most important in practice. Also it turns out yet that for any plastic material certain peaks or valleys exist in the absorption spectrum, which change more strongly by ageing than the remainder of the absorption spectrum; it seems that this is related to the fact that, in ageing, chemical and/or physical changes occur which produce a stronger absorption in a certain spectral area, or that certain compounds disappear, causing the absorption value in certain areas to decrease. As a matter of course, such areas then lend themselves particularly to be employed in the analysis according to the invention. As an example, it can be mentioned that, with a high density polyethylene (HDPE) investigated, which is often used for crates for bottles, such a peak is presented in the area between about 1690 and 1740 cm$^{-1}$ with the greatest changes between 1690 and 1720. It has been found that these changes within the material occur at somewhat different wave numbers than those which occur at the surface and which are therefore observed with the abovementioned prior method which scratches material from the surface. It is believed that, for example, with HDPE, the creation of free radicals (esters) is the most important cause of ageing in a thin surface layer, whilst the creation of carbonyl groups is the main cause of ageing inside. Moreover, the former occurs quite rapidly, the latter only after a longer time. Because it has been established that there is a stronger relationship between the overall mechanical strength and the internal structure of the material, it is believed that the method of this invention, as an ageing test, is more reliable than the one which analyses very thin layers in which the influence of surface phenomena dominates. Crates have been successfully tested by passing IR-radiation through walls having a thickness between 3 and nearly 4 mm.

From the fact that, in the abovementioned very wide area of infrared-radiation, the absorption curve is subject to change in time, it follows that the analysis may be performed with a source which produces infrared radiation in a wide area. It is advantageous, however, to perform the analysis by the use of radiation with a smaller spectral width which then, according to the invention, will be between 10 and 100 cm$^{-1}$, preferably between about 5 and about 40 cm$^{-1}$. In this way existing filters can be employed for measurement at the abovementioned special peaks. Moreover, the measurement may be confined within a spectral area where the absorption curve shows clear changes, so that the information content of the signal obtained will be high.

Furthermore, it is possible to perform a second measurement, in a different wavelength area, which does not overlap the area used with the first measurement, and where the absorption value is not dependent on the state of ageing. In this way an additional criterion for the state of ageing is obtained.

As a matter of course, for the whole detection method a calibration can be performed, which once determines the relationship between the continuously changing absorption values and the limit of acceptability of the related state of ageing on the basis of the mechanical properties of the crate.

The invention also relates to an apparatus for determining the state of ageing of plastic products by means of analysis with infrared radiation, said apparatus comprising at least one source of infrared radiation and one sensor and, furthermore, one carrier for the material to be tested. With this wording the apparatus may be supposed to be used with the prior art method which analysies the scraped off very thin surface layer.

According to the present invention the carrier is adapted for carrying the whole product to be tested and the infrared source and sensor are arranged such that radiation is passed at least through a wall of a product arranged on the carrier. In furtherrance of the speed of treatment this may then be further realized such that the carrier is a line over which the products to be tested can be supplied and discharged. With further preference said line is a conveyor belt. Furthermore it will be clear that with this apparatus signalling means may be connected of any desired type in order to process the result of the detection. More specifically visual or audio signalling may be concerned, so that the operating personnel may interfere. Also it is feasable to stop the line as soon as a product occurs which is inferior and which is to be turned down. Finally it is within the reach of the specialist to process the signalling such that in a conveyor line the acceptable products and the inferior products are separated spatially.

The features of the present invention which are believed to be novel are set forth with particularity in the appended claims.

Said claims and many of the attendant advantages will be more readily appreciated as the same becomes better understood with reference to the following detailed description and considered in connection with the accompanying drawings in which like reference symbols designate like parts throughout the figures.

DESCRIPTION OF THE DRAWINGS

FIG. 1 shows an example of absorption spectra for one and the same plastic material with three different states of ageing;

FIG. 2 diagrammatically gives an elevation of an apparatus installed at a crate conveyor line;

FIG. 3 represents a cross-sectional view according to the arrows III—III of FIG. 2;

DESCRIPTION OF THE METHOD AND OF THE PREFERRED EMBODIMENT OF THE APPARATUS

Figure 4:
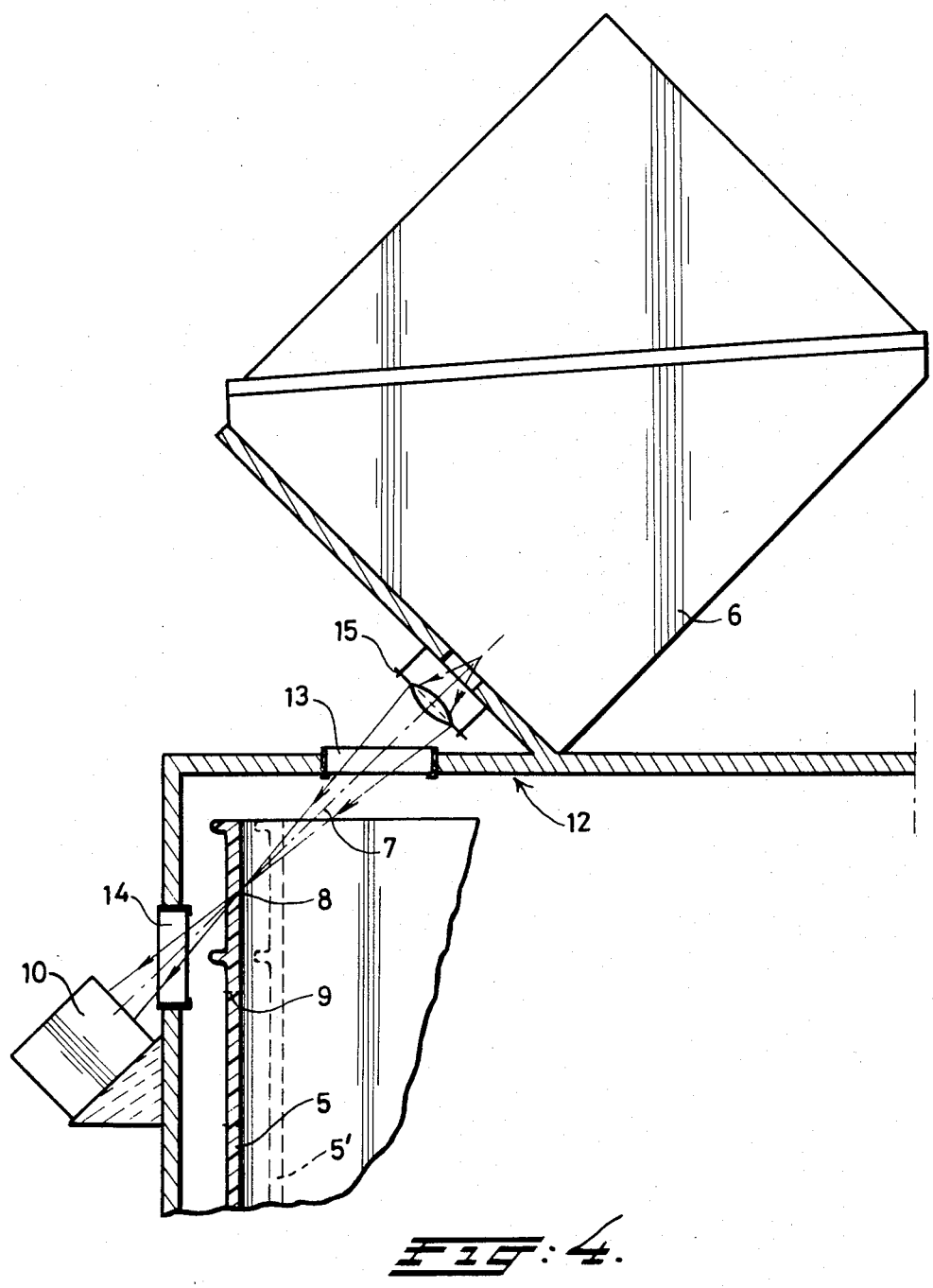
FIG. 4 shows the arrangement of the measuring system proper in more detai and on a larger scale.

In FIG. 1 three absorption curves are visible, corresponding to different states of ageing of high density polyethylene (HDPE)-products of the same composition. For the sake of convenience the three curves have been collected in one figure, but each curve, along the ordinate, has its own zero point. Curve 1 corresponds to a product which is young and which, mechanically, meets all requirements posed. It is visible that generally the absorption values are relatively low.

Curve 2 represents the absorption of a product which, mechanically, is qualified as being "just good". Curve 3 corresponds to a product which turned out to be very bad and must be disqualified.

Generally speaking the course of the absorption spectrum remains the same. Noticeable is the occurance of a set of little peaks, close to one another, which are observed in the end as one single high peak, in the area between about 1690 and 1740 $cm^{-1}$. For the sake of clarity, the area under this peak has been shaded. It is believed that this peak is related to absorption by carbonyl groups which, from the point of view of changing of the chemical and/or physical composition of the synthetic material, originate to the extent that the PE ages. It will therefore be apparent that, in the instance of this material, analysis by radiation having a spectral width for example between 1700 and 1740 $cm^{-1}$ will produce the highest sensivity. It turns out that such specific changes in the absorption for IR-radiation can be found also for synthetic material of different compositions. It also turns out that around 1740 $cm^{-1}$ a smaller peak occurs quite rapidly. This is caused by changes close to the surface, believed to be because of formation of esters. The other peaks, between about 1690 and 1720 $cm^{-1}$ are a more reliable means of testing the inherent mechanical strength as they are observed by radiating through the thickness of the material.

The curves represented in FIG. 1 have been selected such that one may also derive from them the calibration values for the detection. The measurement can be interpreted as follows: all absorption values, in the spectral area used for the measurement, which are lower than the one which corresponds to the peak in curve 2, are accepted and all values higher than the one corresponding to curve 2 will give rise to disqualifying the product in question.

When it concerns checking a series of products in which items occur of a highly varying age, one is less sure that the original chemical composition of all was indeed the same. In order for the method to cope with such different original properties, it deserves preference not to confine oneself to one single wavelength area, but to perform another measurement with a different wavelength value. In the instance of the HDPE to which FIG. 1 relates, one may for this purpose use radiation in the spectral area between 1760 and 1800 $cm^{-1}$. In that case, by comparison of the results of the two measurements in these two spectral areas, additional information becomes available. For each sample one may take the ratio of the absorption values measured in the two areas, but a more clear result will be obtained when taking the logarithm of the ratio of the absorption values in the one and in the other of the spectral areas.

After a description of the method it will be clear that the apparatus or the device for applying the method can be realized in a variety of ways. In order to give an idea, but also in order to illustrate one of the effects of the invention, to wit the fact that non-destructive measurements can be done continuously and quickly, the plan of an apparatus will now be described with reference to FIGS. 2-4. These figures have been kept quite diagammatically.

A conveyor system 4 is represented here, which may be realized entirely in known manner; it has been represented as comprising a plurality of rollers. Crates 5 which are to be tested, stand on this conveyor line. At one side of a crate wall an infrared souce 6 is arranged, that is at such a height above the height of the crates to be tested that the beam, indicated by 7, may pass through the side of wall of crate 5 at the location which is indicated by 8 and which is situated above the aperture 9 where the crate can be gripped. This has to do with the fact that it has turned out that the sensitivity for ageing phenomena is highest at the location above this aperture. At the other side of the crate wall there is an infrared sensor 10, which is connected to a processing and display device 11.

FIG. 4 ia a partial cross-section through the apparatus, showing the measuring arrangement at a larger scale and in some more detail. The wall of a crate 5 is visible, including the grip aperture 9 and the location above this aperture, indicated by 8 like in FIG. 3, where the beam 7 of infrared radiation passes through the crate wall. In order to protect the infrared transmitter 6 and the detector 10, a shielding structure 12 is provided on top of the crate and beside the crate. This structure 12 contains two windows 13 and 14 which transmit infrared energy. The shielding structure 12 may at the same time be a supporting structure for the transmitter 6 and the detector 10. FIG. 4 shows that, with an arrangement of transmitter and detector such that the infrared beam is oriented under an angle of about 45°, it is well possible to pass the beam at the location 8 through the crate wall and the dimensions may even be such that a certain tolerance in lateral direction as regards the exact position of the crate 5 is acceptable; the crate 5' represented in broken lines, shows that the beam will still pass through the crate wall.

At some other appropriate location along the conveyor 4, there may be an arrangement (not represented) of means such as nozzles, which blow jets of air against the crate wall in order to remove any dirt and particularly liquids, especially from the region where the ageing test is to be performed. Water and oil absorb a considerable amount of infrared energy and would therefor be a cause of incorrect measurement.

Furthermore, there may be some provision to mechanically or optically determine the presence of a crate at the place where the ageing test is to be performed. These means may be used to control switching on or off of the measuring system.

In connection with the description of the method there was a reference to making two measurements. This can be done in different ways. The two measurements can be simply made simultaneously. As a matter of course, appropriate filters will be arranged between the infrared sources and the associated sensors, such filters being adapted to the spectral are a desired for the analysis, supposing infrared sources of the type which produces radiation in a wide spectral area. In general, the determination may then be performed in an area having a width between 5 and 100 cm$^{-1}$. More particularly, a width may be chosen between 5 and 40 cm$^{-1}$; this corresponds to the effective transmission width of commercially available filters. As an alternative one might also use sources, such as lasers, the radiation of which have a limited spectral width already, in many cases the width of one or a plurality of so-called spectral lines. Again, another possibility is that use is made of one single source employing two filters, either by performing the two different measurements in time sequence, or by splitting the beam and passing the halves to the individual optical paths for the two measurements.

The infrared transmitter such as 6, may be realized by employing a commercially available infrared analyser, the 937 MIRAN Analyser. This transmitter is a single beam spectrometer, capable of measuring the infrared transmission of a sample at two fixed wavelengths.

The major components are a radiation source, collector mirror, mechanical chopper, cam switched interference filters, pyroelectric detector and primary signal processing electronics.

In operation, infrared energy from the source is concentrated by a concave mirror, chopped by a rotating disk, and focussed onto a slit after passing through two narrow band interference filters which are alternately positioned in the beam.

With the present invention for HDPE-testing filters are used with a maximum transmission at respectively 1765 cm$^{-1}$ and 1720 cm$^{-1}$ and with bandwidth of approximately 20 cm$^{-1}$. In this way the infrared beam is modulated in time (chopper) and wavelength (switching filters), passed through the sample and is then focussed onto the pyroelectric detector 6 by means of a lens. After pre-amplification the detector signal is demodulated into a sample ($E_s$) and a reference ($E_r$) signal representing the transmission values of the sample at respectively 1720 cm$^{-1}$ and 1765 cm$^{-1}$. These two signals are transmitted by means of two current loops to a control module. In the control module $E_s$ and $E_r$ are multiplexed through a logarithm amplifier to produce two signals representing the $-\log E_s(=A_s)$ and the $-\log E_r(=A_r)$. By means of a differential amplifier the signal $A_r$ is substracted from $A_s$ giving a signal $(=A_m)$ proportional to the difference between the absorbance at 1720 cm$^{-1}$ and 1765 cm$^{-1}$ of the sample.

From this signal an adjustable offset is substracted (zero calibration) and the resulting signal is amplified with an adjustable factor to meet an optimum measuring range (span calibration). The final signal is fed to the digital display on front panel 11 and to a standard output terminal strip. Moreover the control module is equipped with some diagnostic electronics to indicate failures in the measurements.

Normally, with the MIRAN Analyser, the pre-amplification of the detector signals $E_s$ and $E_r$ is adjusted in such a way that without a sample in the beam (100% transmission) the absorbance signals $A_s$ and $A_r$ in the control module become zero.

In the case of testing crates, the expected transmission values are between 0% and 10%. This low transmission range, together with the limited span of the log amplifier, will result in a small usable absorbance range. Therefore, the amplification factors for both signals are chosen such that for a sample with a very low carbonyl content, the absorbance signals $A_s$ and $A_r$ become approximately zero. In doing so, the full span of the log amplifier becomes available for the measurements. Because of the difference in amplification factor for $E_s$ and $E_r$, offsets are introduced in $A_s$ and $A_r$ which result in a constant offset in the carbonyl output signal ($A_m$) relationship. In practise this offset doesn't cause any difficulties. All measurements are done with the fastest response time possible.

For the particular purpose in connection with the present invention adaption of the commercially available analyser in two respects is desirable. In the first place the standard available free path length, which is about 5 cm, is to be increased to about 20 cm. This can be done by arrangement of an additional lens in the optical path of the infrared beam, this lens being indicated by 15 in FIG. 4.

Furthermore, it might be desirable to adapt the testing device or apparatus to rather high conveyor speeds in commercial crate conveying systems. For these high speed conveyors it is desirable to adapt the response time of the analyser, which can be done by changing the electronics in a way which will cause no questions to the specialist. For example, a response time of the standard analyser being 1.5 second, it might be lowered to 0.5 or 1 second. This will imply an increase of the noise level. The noise is inversely proportional to the square route of the response time. In connection with the ageing test, however, this increased noise level will not cause any serious problems.

What is claimed is:

1. Method of determining the state of ageing of plastic products comprising the steps of passing infrared radiation through the product determining the absorption thereof in the material at a wavelength value selected at the spectral location where the chemical and/or physical change in the plastic created by ageing causes a change in absorption, performing a second measurement in a different wavelength area where the absorption value is independent of the state of ageing, and comparing the difference between the absorption value and the value of said second measurement to obtain a pre-adjusted calibration value as a criterion for determining the state of ageing.

2. Method of selecting aged plastic products out of a collection, comprising passing infrared radiation through each product, determining the infrared absorption value in the material, comparing this absorption with a pre-established value and producing a signal representative for the difference of the two values, and utilizing such signal to control a selection means for the products.

3. Apparatus for determining the state of ageing of plastic products, comprising at least one source of infrared radiation and one sensor carrier means adapted for carrying the whole product to be tested, the infrared source and sensor being positioned so that radiation from the source to the sensor is passed at least through a wall of a product supported on the carrier.

4. Apparatus according to claim 3, wherein the carrier is a line over which the product to be tested can be supplied and discharged.

5. Apparatus according to claim 3, wherein the carrier is a conveyor belt.

6. Apparatus according to claim 3, wherein the infrared source is of a type which produces radiation in a wide spectral area.

7. Apparatus according to claim 6 further comprising a filter positioned in the optical path between said infrared source and the sensors.

8. Apparatus according to claim 3, wherein the infrared source is of a type which produces radiation in a wide spectral area, between said source and the sensors further comprising two filters positioned in the optical path.

9. Apparatus according to claim 3, wherein the infrared source is of a type which produces one or a plurality of distinct spectral lines.

10. Apparatus according to claim 3, wherein two sources are provided, each producing infrared radiation in a desired narrow spectral area, there being one single sensor to receive the radiation from the two sources.

11. Apparatus according to claim 3, wherein two sources are provided, each producing infrared radiation in a desired narrow spectral area, and two sensors positioned to receive the radiation from said two sources.

12. Apparatus for determining the state of ageing of plastic products comprising a supporting and shielding structure arranged above and beside a supply and discharge line for the products, said shielding structure having an infrared transmitter and filtering device on the one hand and the associated detector device on the other hand, infrared transparant windows in said shielding structure, said is to being infrared radiation is transmitted through the windows and through a wall of each of the products passing on the line.

13. Apparatus according to claim 12, further comprising means for cleaning the products before they reach the area of the windows where the infrared test is performed.

14. Method of determining the state of ageing of high-density polyethylene products, comprising passing infrared radiation having a spectral value between 1690 and 1740 cm$^{-1}$ through the product and determining the absorption of the radiation by the material of the product, repeating for the same product at a spectral value outside the area from 1690 thru 1740 cm$^{-1}$ the steps of determining a predetermined relationship between the two absorption values, and comparing the result with a calibration value of said predetermined relationship.

15. The method of determining the state of ageing of plastic products non-destructively comprising passing infrared radiation through the product, the wavelength value of the radiation to be measured being selected at a spectral location where the chemical and/or physical change in the plastic created by ageing causes a change in absorption, and determining the absorption in the material and utilizing said absorption as a criterion for the state of ageing.

16. The method of determining the state of ageing of plastic products as claimed in claim 15 wherein the absorption in the material is determined utilizing the comparative difference between the absorption value and a preadjusted value as a criterion for the state of ageing.

* * * * *